US010445891B2

(12) United States Patent
Wyeth

(10) Patent No.: US 10,445,891 B2
(45) Date of Patent: Oct. 15, 2019

(54) MEDICAL IMAGE PROCESSING APPARATUS AND METHOD

(71) Applicant: Toshiba Medical Systems Corporation, Otawara-shi (JP)

(72) Inventor: Daniel Lee Catherwood Wyeth, Edinburgh (GB)

(73) Assignee: Canon Medical Systems Corporation, Otawara-shi (JP)

( * ) Notice: Subject to any disclaimer, the term of this patent is extended or adjusted under 35 U.S.C. 154(b) by 111 days.

(21) Appl. No.: 15/802,675

(22) Filed: Nov. 3, 2017

(65) Prior Publication Data
US 2019/0139238 A1  May 9, 2019

(51) Int. Cl.
*G06T 7/33* (2017.01)
*G06T 7/73* (2017.01)
(Continued)

(52) U.S. Cl.
CPC .............. *G06T 7/337* (2017.01); *A61B 5/055* (2013.01); *A61B 6/032* (2013.01); *A61B 6/037* (2013.01);
(Continued)

(58) Field of Classification Search
CPC ................................................... G06T 3/0056
See application file for complete search history.

(56) References Cited

U.S. PATENT DOCUMENTS

| 7,583,857 B2* | 9/2009 | Xu ....................... G06K 9/3216 358/450 |
| 2007/0265525 A1* | 11/2007 | Sun ......................... A61B 5/055 600/420 |

(Continued)

FOREIGN PATENT DOCUMENTS

| JP | 2010-253058 A | 11/2010 |
| JP | 2015-198907 A | 11/2015 |

OTHER PUBLICATIONS

"AutoAlign" Siemens Healthineers United Kingdom, 2019, https://www.healthcare.siemens.co.uk/magnetic-resonance-imaging/options-and-upgrades/clinical-applications/autoalign, 2 page (Year: 2019).*
(Continued)

*Primary Examiner* — Gandhi Thirugnanam
(74) *Attorney, Agent, or Firm* — Oblon, McClelland, Maier & Neustadt, L.L.P.

(57) ABSTRACT

An apparatus comprises processing circuitry configured to: obtain medical imaging data that is representative of an anatomical region of a subject, the anatomical region comprising at least one anatomical feature of interest; obtain a template that is representative of a desired view of the at least one anatomical feature of interest; register the medical imaging data and reference anatomical data to obtain a distribution of registration probability with respect to at least one registration parameter; and perform a selection process comprising: obtaining a plurality of transforms, each having an associated registration; for each of the plurality of transforms: generating a respective view of the at least one anatomical feature of interest based on said transform; and determining a template matching probability that represents a similarity of the generated view to the template; and selecting at least one of the transforms and/or at least one of the views based on a combination of at least one of the registration probabilities with at least one of the template matching probabilities.

20 Claims, 6 Drawing Sheets

(51) Int. Cl.
  *G06T 3/00*   (2006.01)
  *G06T 7/37*   (2017.01)
  *A61B 6/03*   (2006.01)
  *A61B 6/00*   (2006.01)
  *A61B 8/08*   (2006.01)
  *A61B 5/055*  (2006.01)

(52) U.S. Cl.
  CPC .......... *A61B 6/4085* (2013.01); *A61B 6/5229* (2013.01); *A61B 8/5238* (2013.01); *G06T 3/0006* (2013.01); *G06T 3/0056* (2013.01); *G06T 7/37* (2017.01); *G06T 7/74* (2017.01); *G06T 2207/30008* (2013.01)

(56) References Cited

U.S. PATENT DOCUMENTS

2016/0018489 A1*  1/2016  Farivar-Mohseni ........................ G01R 33/34084 600/422
2016/0180521 A1*  6/2016  Mountney ................ A61B 6/12 382/131
2017/0358071 A1* 12/2017  Yamaoka ................ G06T 7/337
2019/0005661 A1*  1/2019  Steinle ...................... G06T 7/33
2019/0139238 A1*  5/2019  Wyeth ..................... G06T 7/337

OTHER PUBLICATIONS

Mohammad A. Dabbah, et al., "Detection and location of 127 anatomical landmarks in divers CT datasets" Proc. of SPIE, vol. 9034, 2014, pp. 1-11 (Year: 2014).*

"AutoAlign" Siemens Healthineers United Kingdom, 2017, https://www.healthcare.siemens.co.uk/magnetic-resonance-imaging/options-and-upgrades/clinical-applications/autoalign, 1 page.

Mohammad A. Dabbah, et al., "Detection and location of 127 anatomical landmarks in divers CT datasets" Proc. of SPIE, vol. 9034, 2014, pp. 1-11.

* cited by examiner

MEDICAL IMAGE PROCESSING APPARATUS AND METHOD

FIELD

Embodiments described herein relate generally to processing medical images, for example to an apparatus and method for processing medical image data to obtain a desired view of an anatomical feature, for example a joint.

BACKGROUND

It is known to use one or more medical imaging techniques to obtain radiological data relating to a patient or other subject, and to process the medical imaging data to obtain medical images.

Many radiological workflows may depend on oblique reformats. An oblique reformat may comprise a multi-planar reformat of volumetric imaging data that is performed for a selected plane that is not one of the principal anatomical planes (which may comprise coronal, sagittal and axial planes). An oblique reformat may be obtained by resampling at least part of the volumetric imaging data set onto the selected plane.

An oblique reformat may comprise a two-dimensional image displayed as if viewed from a given angle. An oblique reformat may be oriented to show clinically significant anatomy in a standard perspective. An oblique reformat may comprise a series of images. The images may be parallel to each other. The images may be orthogonal to a principal axis of view. The principal axis of view may be a line between an observer and the anatomy of interest.

Oblique reformats may be used, for example, in musculoskeletal (MSK) studies of joints in the shoulder, pelvis and knee. The focus in some such studies may be the position of one bone in a cavity, as viewed from a very specific angle.

Oblique reformat views (for example, of joints) may be time consuming and/or difficult to construct manually. Oblique reformat views may also be difficult to construct automatically. Oblique reformat views may often be at least partially determined by the tangent to a smooth, curved surface. In some circumstances, such a tangent may be difficult to compute automatically.

Oblique reformat views may often be variable between patients. For example, different patients may need to be viewed from different angles in order to ensure that the orientation of specific anatomical structures best supports diagnosis. Different patients may have variability in their anatomy that may lead to different views being used.

Furthermore, different clinicians may have different viewing preferences. For example, different clinicians may wish to view a patient's anatomy from slightly different angles.

BRIEF DESCRIPTION OF DRAWINGS

Embodiments are now described, by way of non-limiting example, and are illustrated in the following figures, in which.

DETAILED DESCRIPTION

Certain embodiments provide an apparatus comprising processing circuitry configured to: obtain medical imaging data that is representative of an anatomical region of a subject, the anatomical region comprising at least one anatomical feature of interest; obtain a template that is representative of a desired view of the at least one anatomical feature of interest; register the medical imaging data and reference anatomical data to obtain a distribution of registration probability with respect to at least one registration parameter; and perform a selection process comprising: obtaining a plurality of transforms, each having an associated registration probability; for each of the plurality of transforms: generating a respective view of the at least one anatomical feature of interest based on said transform; and determining a template matching probability that represents a similarity of the generated view to the template; and selecting at least one of the transforms and/or at least one of the views based on a combination of at least one of the registration probabilities with at least one of the template matching probabilities.

Certain embodiments provide a method comprising: obtaining medical imaging data that is representative of an anatomical region of a subject, the anatomical region comprising at least one anatomical feature of interest; obtaining a template that is representative of a desired view of the at least one anatomical feature of interest; registering the medical imaging data and reference anatomical data to obtain a distribution of registration probability with respect to at least one registration parameter; performing a selection process comprising: obtaining a plurality of transforms, each having an associated registration probability; for each of the plurality of transforms: generating a respective view of the at least one anatomical feature of interest based on said transform; and determining a template matching probability that represents a similarity of the generated view to the template; and selecting at least one of the transforms and/or at least one of the views based on a combination of at least one of the registration probabilities with at least one of the template matching probabilities.

Figure 1:
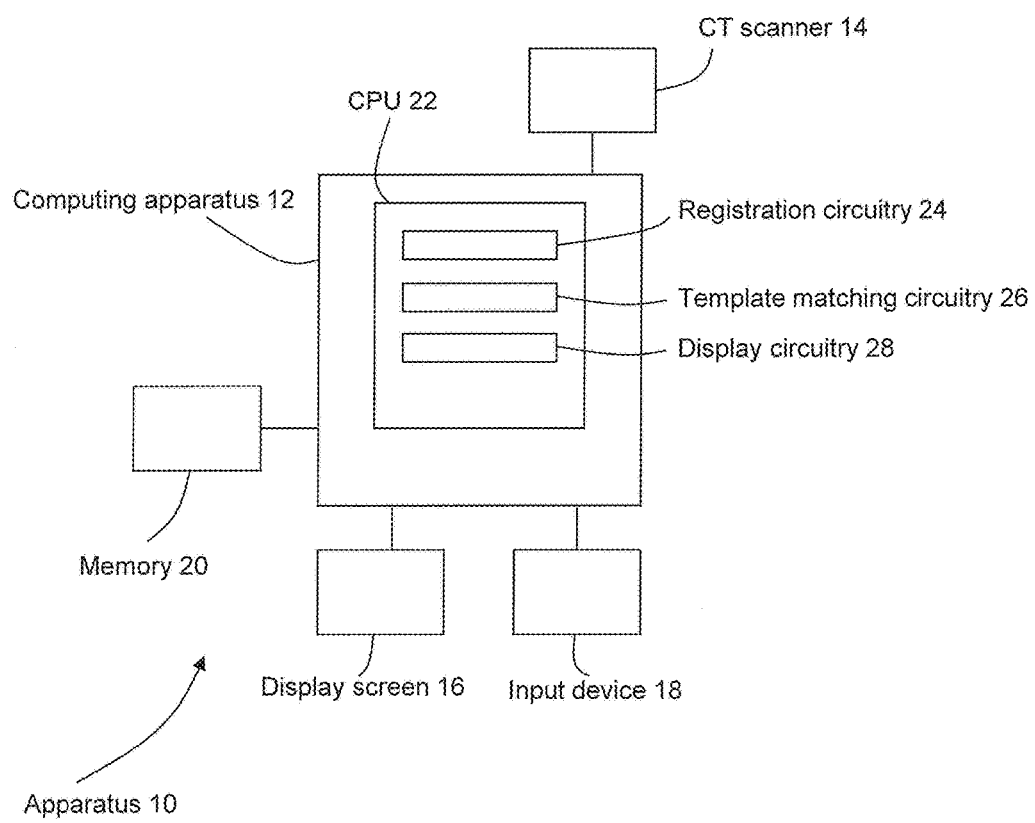
FIG. 1 is a schematic diagram of an apparatus according to an embodiment.

An apparatus 10 according to an embodiment is illustrated schematically in FIG. 1.

The apparatus 10 comprises a computing apparatus 12, in this case a personal computer (PC) or workstation, which is connected to a computed tomography (CT) scanner 14, one or more display screens 16 and an input device or devices 18, such as a computer keyboard, mouse or trackball. In other embodiments, the computing apparatus 12 may not be connected to the CT scanner 14.

The CT scanner 14 may be any CT scanner that is configured to obtain volumetric medical imaging data that is representative of at least one anatomical feature of a patient or other subject. In the present embodiment, the anatomical feature is the shoulder. In other embodiments, the anatomical feature may be a different joint, for example the hip, knee or elbow. In further embodiments, the volumetric imaging data may be representative of any anatomical feature or features. For example, the volumetric imaging data may be representative of any appropriate bone or organ.

In alternative embodiments, the CT scanner 14 may be replaced or supplemented by a scanner configured to obtain imaging data in any other imaging modality, for example a cone-beam CT scanner, MRI (magnetic resonance imaging) scanner, X-ray scanner, ultrasound scanner, PET scanner (positron emission tomography) or SPECT (single photon emission computed tomography) scanner. The imaging data may be two- or three-dimensional. In some embodiments, three-dimensional imaging data may be obtained by acquiring multiple two-dimensional scans.

In the present embodiment, volumetric imaging data sets obtained by the CT scanner 14 are stored in memory 20 and subsequently provided to computing apparatus 12. In an alternative embodiment, volumetric imaging data sets are supplied from a remote data store (not shown) which may form part of a Picture Archiving and Communication System (PACS). The memory 20 or remote data store may comprise any suitable form of memory storage.

Computing apparatus 12 provides a processing resource for automatically or semi-automatically processing imaging data sets, and comprises a central processing unit (CPU) 22.

The computing apparatus 12 includes registration circuitry 24 configured to register a volumetric medical imaging data set with a reference anatomical data set and to output a probability distribution; template matching circuitry 26 configured to match a template to a two-dimensional image patch obtained from the volumetric medical imaging data set; and display circuitry 28 configured to display a selected image on display 16.

In the present embodiment, the circuitries 24, 26, 28 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
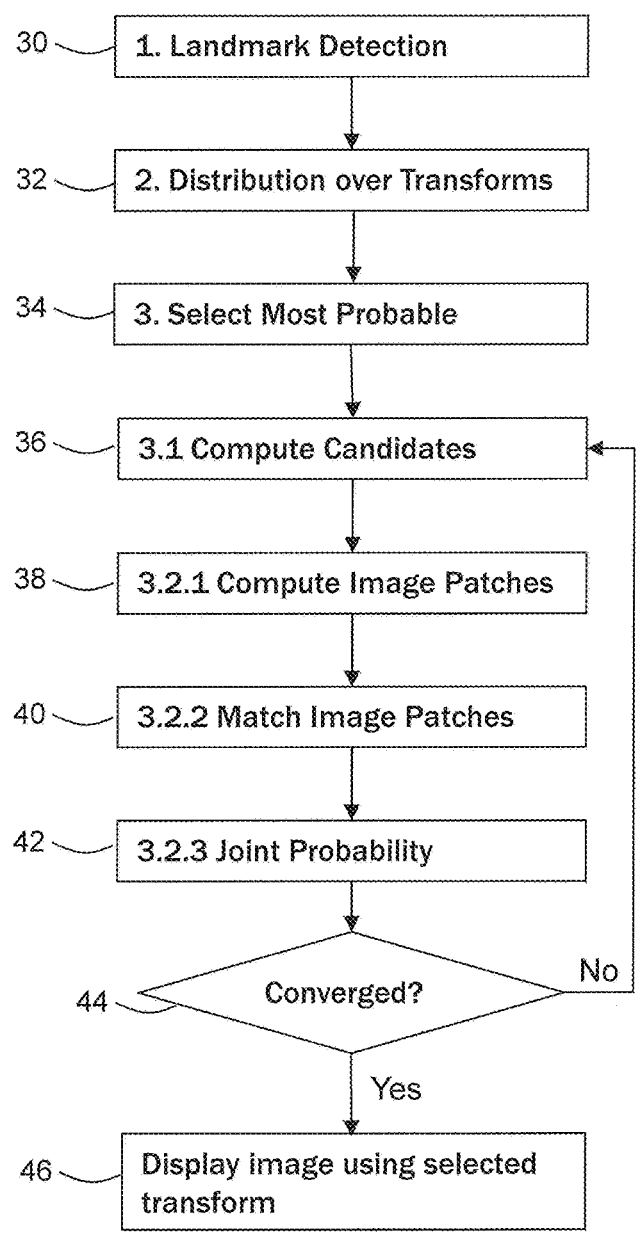
FIG. 2 is a flow chart illustrating in overview a method of an embodiment.

FIG. 2 is a flow chart illustrating in overview a method for automatically constructing and displaying an oblique reformat of a volumetric medical imaging data set. In the present embodiment, the oblique reformat is such as to show a desired view of a shoulder joint of a patient. In the method of FIG. 2, registration of the volumetric medical imaging data set to a set of reference data is combined with a template matching process which matches each of a series of image patches generated from the volumetric medical imaging data set to a template that is representative of the desired view of the shoulder joint. In some circumstances, use of a template matching process may provide a better view of the shoulder joint than may be provided if the view were obtained by registration alone.

At stage 30, the registration circuitry 24 receives a set of imaging data that is representative of an anatomical region of a patient. The anatomical region comprises at least one anatomical feature of the subject that is of interest. In the present embodiment, the anatomical region comprises the shoulder of the patient and surrounding anatomy. In further embodiments, the registration circuitry 24 may receive imaging data that is representative of any anatomical feature or features of a subject, for example any joint, bone or organ of the subject. The subject may be human or veterinary.

The set of imaging data may also be referred to as an image volume. In the present embodiment, the imaging data is a volumetric CT data set. In other embodiments, any suitable type of imaging data may be used.

The registration circuitry 24 detects a plurality of landmarks in the set of imaging data. Anatomical landmarks may be recognizable points within the body's structure, for example well defined points on bones, organs or other anatomical structures.

In some embodiments, the method of landmark detection is as described in, for example, Mohammad A Dabbah, Sean Murphy, Hippolyte Pello, Romain Courbon, Erin Beveridge, Stewart Wiseman, Daniel Wyeth and Ian Poole, Detection and location of 127 anatomical landmarks in diverse CT datasets', Proc. SPIE 9034, Medical Imaging 2014: Image Processing, 903415 (Mar. 21, 2014); doi:10.1117/12.2039157, which is hereby incorporated by reference. In other embodiments, any landmark detection method may be used.

At stage 32, the registration circuitry 24 obtains a set of reference anatomical data comprising a plurality of reference landmark locations. In the present embodiment, the plurality of reference landmark locations comprises locations for 127 anatomical landmarks described in Dabbah et al as referenced above. In other embodiments, locations for any appropriate landmarks may be used.

In the present embodiment, the reference landmark locations are locations for landmarks in an anatomical atlas, which in the present embodiment is a synthetic atlas. The locations of the landmarks in the anatomical atlas may have been previously been determined by an expert, or may have been obtained by any suitable method. In other embodiments, the reference landmark locations may be locations of landmarks in any suitable reference data set, for example any suitable atlas or virtual anatomy.

At least some of the reference landmark locations at stage 32 correspond to the same well-defined points on anatomical structures as are detected in stage 30. For example, a set of thoracic landmarks may be marked in the synthetic atlas and corresponding thoracic landmarks may be detected in the imaging data set.

Given the locations of corresponding landmarks in the image volume (from stage 30) and in the atlas (from stage 32), the registration circuitry 24 performs a registration process. The registration process comprises registering together the landmarks in the image volume and the landmarks in the atlas. The registration process may be referred to as a point-based registration.

The detected landmarks comprise at least three non-collinear landmarks for which locations of corresponding landmarks are provided in the reference anatomical data. At least three non-collinear points may be used to fully determine the orientation of a 3D object in a 3D space. Any suitable number of landmarks may be used.

In the present embodiment, the registration process comprises an affine registration. The affine registration may comprise translation, rotation and/or scaling. The scaling may be anisotropic. In the present embodiment, an iterative least squares method is used. In other embodiments, any suitable registration process may be used, for example any point-based registration. In some embodiments, the registration uses splines or deformation. In some embodiments, the registration process comprises non-rigid registration.

In the present embodiment, a relation between the locations of the landmarks detected at stage 30 and the locations of the landmarks in the atlas is modelled using Bayesian linear regression. The relation between the detected and atlas landmarks is modelled by a linear transform plus Gaussian noise.

A linear model is assumed with:

$y = \phi x + \in$, with $\in \sim \mathcal{N}(0; \sigma^2)$ where y represents the locations of the detected landmarks in the imaging set, x represents the locations of the corresponding landmarks in the atlas, $\phi$ is the transform between the coordinate space of the imaging data set and the coordinate space of the atlas, and $\in$ is a Gaussian distibution of noise having a mean of 0 and a variance of $\sigma^2$.

A probability distribution for the location of the set of detected landmarks y given their corresponding reference landmarks locations x under a particular transform $\phi$ may be written as:

$$P(y \mid \phi, x, \sigma_x) = \frac{1}{\sqrt{2\pi\sigma_x^2}} e^{-\frac{1}{2\sigma_x^2} \sum_i (y_i - \phi x_i)^2}$$

The expression on the right is the conditional probability of the set of detected landmarks y given their corresponding reference landmarks locations x under a particular transformation $\phi$.

The probability distribution above comprises a univariate Gaussian distribution over the error between the detected point $y_i$ and transformed reference $\phi x_i$. This may be considered to be a simple formulation of the probability of y in terms of $\phi$.

In other embodiments, the noise may be modelled with any appropriate function. For example, the noise may be modelled with a multivariate Gaussian, in which there is a separate mean and variance for the error with respect to each parameter in the transform $\phi$. Using a multivariate Gaussian may reflect the fact that some parts of the transform (for example, the scale) may be known with greater certainty than other parts of the transform. In such embodiments, the distribution is not modelled over the raw error between detected and transformed reference landmarks. Instead, the error in each parameter of the candidate transform is used. The method may quantify the difference between the candidate transform and the simplest variant of the candidate transform that perfectly maps a reference landmark to its corresponding detected landmark.

If the transform is indicated by $\Phi(x, y)$ then a multivariate Gaussian adapted to this use case may be written as:

$$P\left(y \mid \phi, x, \sum\right) = \frac{1}{\sqrt{|2\pi\Sigma|}} e^{-\frac{1}{2}(\Phi(x,y)-\phi)\Sigma^{-1}(\Phi(x,y)-\phi)}$$

where $\phi$ is the vector of parameters for the candidate transform, $\Sigma$ is the covariance matrix of these parameters of $\phi$, and $\Phi(x, y)$ is the parameterisation of the ideal transform mapping x to y, where this is a vector in the same form as the parameterisation $\phi$. The error is computed for each parameters of the transform using its own variance. Different errors may use different scales. The different scales may have the effect of different errors having different weights.

The probability distribution for the landmark location above may be used to obtain a probability distribution for the transform $\phi$ given the location y of the landmark in the volumetric imaging data set, the location x of the corresponding reference landmark in the atlas, and the variance $\sigma_x^2$, $P(\phi \mid y, x, \sigma_x^2) \propto P(y \mid \phi, x, \sigma_x^2) P(\phi \mid x, \sigma_x^2) \propto P(y \mid \phi, x, \sigma_x^2) P(\phi)$ where $P(\phi \mid x, \sigma_x^2) = P(\phi)$ because $\phi \perp x$ and $\phi \perp \sigma^2$.

If we assume that $\phi \sim \mathcal{N}(\mu^2, \sigma_\phi^2)$ then we obtain $$P(\phi \mid y, x, \sigma_x^2, \sigma_\phi^2) \propto \frac{1}{2\pi\sigma_x\sigma_\phi} e^{-\frac{1}{2} \sum_i \left[ \frac{(y_i - \phi x_i)^2}{\sigma_x^2} + \frac{(\phi - \mu_\phi)^2}{\sigma_\phi^2} \right]}$$

In some embodiments, $$\frac{(y_i - \phi x_i)^2}{\sigma_x^2} \text{ and } \frac{(\phi - \mu_\phi)^2}{\sigma_\phi^2}$$

are vector quantities having different dimensionalities. There exists a metric $\delta$: $T \to \mathbb{R}$ which maps the difference between the candidate transform and the mean to a scalar value, $$\frac{\delta(\phi - \mu_\phi)^2}{\sigma_\phi^2}.$$

In the present embodiment, a probability distribution is obtained using Bayesian linear regression. In other embodiments, any registration process may be used that outputs a probability distribution.

The probability distribution may be referred to as a probability distribution over transforms, or a probability distribution over values of transform parameters. The probability distribution may be considered to provide a respective registration probability for each of a plurality of registrations, each having a different transform. Each different transform has different values for a set of transform parameters, which in the present embodiment comprise translation, rotation and scaling parameters.

The registration method of the present embodiment may differ from some known registration methods in that a probability distribution is obtained instead of a single transform. For example, one known method of registration uses linear regression on the transform parameters to minimise the squared error, which may produce a single set of transform parameter values and not a probability distribution.

In other embodiments, any registration method that produces a distribution of registration probabilities may be used, for example any registration method that may be considered to agree with a best fit between landmarks. Any appropriate combination of a registration method (for example, iterative optimisation of mutual information) with landmarks may provide a probability distribution. The probability distribution may be obtained from modelling the error in the application of the transformation to the landmarks. A condition may be imposed that the modelling agrees reasonably well with the transform that one may obtain by performing least squares on the landmarks. This may allow an error having zero mean to be assumed.

The use of a probability distribution may allow the information from the landmark correspondences to be combined with other inputs.

Figure 3:
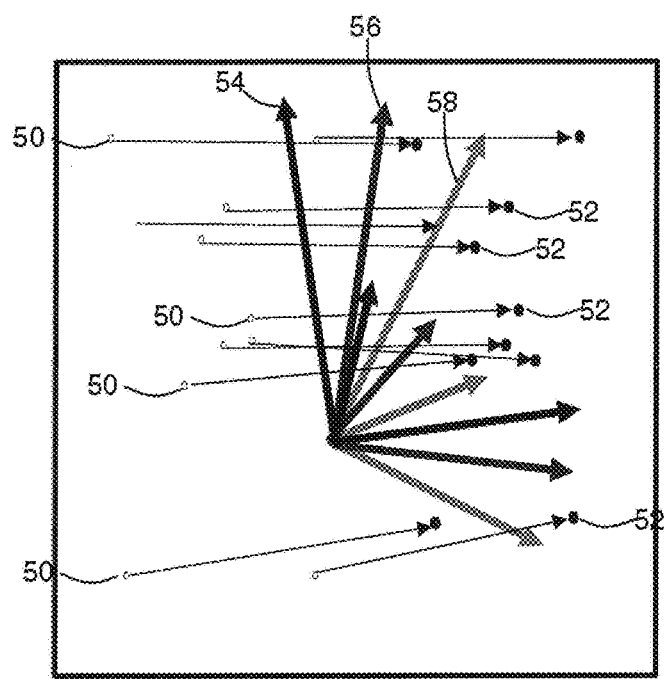
FIG. 3 is a schematic diagram representing possible transforms.

FIG. 3 represents three possible transforms that are sampled from the probability distribution determined by the correspondence between landmarks. Open dots 50 represent a set of landmarks detected in an image volume. Closed dots 52 represent reference landmarks, for example landmarks in an atlas. A first possible transform between the landmarks and the reference landmarks is represented by a first set of arrows 54. A second possible transform is represented by a second set of arrows 56. A third possible transform is represented by a third set of arrows 58.

In FIG. 3, decreasing probability is represented by decreasing opacity of the sets of arrows. The first transform has the highest probability, which is represented by high opacity of the first arrows 54. The second transform has a lower probability, which is represented by lower opacity of the second arrows 56. The third transform has the lowest probability, which is represented by low opacity of the third arrows 58.

At stage 34, the registration circuitry 24 selects the most probable registration from the registration probability distribution. The most probable registration may be the registration that transforms the imaging data in accordance with the set of transform parameter values having the highest registration probability (which may also be referred to as the most probable transform). In the following discussion, we will discuss different registrations by referring to the transforms associated with those registrations. In the present embodiment, the transforms are affine transforms.

After selecting the most probable transform, the registration circuitry 24 begins a process of searching through the transforms in the probability distribution, starting with the most probable transform.

At stage 36, the registration circuitry 24 generates further candidate transforms by sampling further values for each of the transform parameters in the most probable transform. Sampling further values for each of the transform parameters may comprise adjusting a current value for a transform parameter to obtain one or more different values for that transform parameter, which may be described as neighbouring values.

In the present embodiment, the registration circuitry 24 generates two new candidate transforms for each parameter of the transform (for example, for each translation parameter, rotation parameter and scaling parameter). For each parameter, a first new candidate transform is generated by subtracting a fixed value from the value for the parameter in the most probable transform. A second new candidate transform is generated by adding the fixed value to the value for the parameter in the most probable transform. The resulting number of candidate transforms is 2n+1 where n is the number of parameters in the transform $\phi$.

In other embodiments, new candidate transforms may be obtained by updating the value for each parameter in the most probable transform by a fixed probability threshold. It may be possible to update the values by a fixed probability threshold because the gradient of the probability distribution with respect to each transform parameter may be known from the probability distribution. In further embodiments, any suitable method may be used for generating the new candidate transforms. New candidate transforms may be obtained by sampling values neighbouring a current value for any one of the transform parameters, or any combination of transform parameters.

In some embodiments, a gradient descent approach may be used to search through the transform parameters. The process may select new candidate transforms by following the steepest gradient. The gradient descent approach is discussed further below.

The output of stage 36 is a set of candidate transforms. The set of candidate transforms comprises the most probable transform and the further candidate transforms that have been obtained by sampling parameter values neighbouring the parameter values in the most probable transform. In the present embodiment, the set of candidate transforms comprises 2n+1 candidate transforms, where n is the number of parameters in the transform $\phi$.

At stage 38, the registration circuitry 24 processes the imaging data set to obtain a respective view for each of the candidate transforms that was output at stage 36. The view comprises two-dimensional image data. The view may also be referred to as a 2D image, 2D image patch, candidate 2D image or candidate image region. The view may be referred to as an image or image patch even though in many circumstances it may not be displayed to a user, and even though it relates to a subset of the imaging data set rather than to the imaging data set as a whole.

In the present embodiment, each view comprises a respective oblique reformat of the imaging data set.

The registration circuitry 24 stores a protocol, which may be definable by a user. The protocol comprises a specification for obtaining a desired oblique reformat view of the shoulder. The protocol may comprise, for example, a template image, a matrix specifying a position and orientation of a bounding box, and some dimensions specifying a size of the bounding box. The protocol may comprise some display parameters, for example window level.

In other embodiments, the registration circuitry 24 may store one or more protocols for obtaining desired views of any suitable anatomy.

Figure 4:
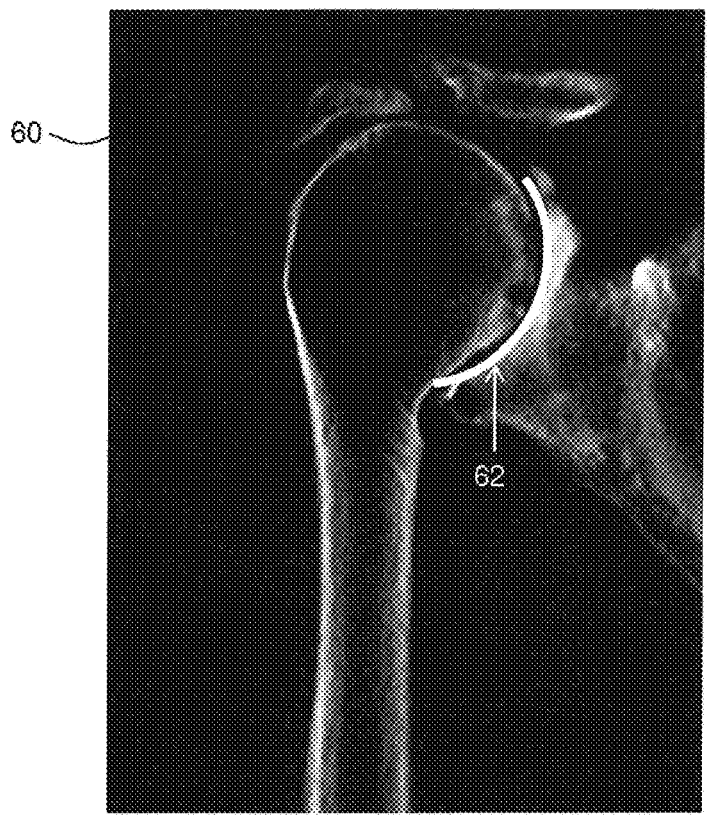
FIG. 4 is an oblique reformat image of a shoulder joint.

FIG. 4 shows an oblique reformat image 60 of a shoulder from a perspective that shows the glenoid cavity 62 between the scapula and the head of the humerus. The perspective of FIG. 4 may be considered to be a desired, or required, perspective for viewing the shoulder joint. In the present embodiment, the protocol stored by the registration circuitry 24 is a protocol for producing an oblique reformat as shown in FIG. 4.

The protocol defines the position and orientation of a box. In the present embodiment, the box is positioned such that the target anatomy (in this case, the shoulder) is at the centre of the box. The protocol also defines how the box is bounded. The protocol defines the size and shape of the box. In the present embodiment, the bounding box is specified by the coordinates of its vertices. In other embodiments, the bounding box may be specified in any suitable manner, for example by using one vertex, a vector for the orientation and the dimensions along each axis.

The protocol also defines at least one image plane within the box. In the present embodiment, an image plane is defined in the centre of the box. For example, the image plane may be positioned in the centre of one axis of the box, and may extend across the full size of the box with respect to the other two axes of the box. In other embodiments, the image plane or planes may be defined in any suitable manner.

In the present embodiment, the target anatomy on which the box is centred is the shoulder. The protocol describes the position, orientation and bounds of the box relative to reference anatomical data, which in the present embodiment is the atlas that was also used in registration of the landmarks. The box is oriented so that the intersection of the target anatomy with the centre plane in a reformat defined using the box shows the anatomy (in this case, the shoulder) from a required perspective. The box may be arbitrarily aligned. In some embodiments, the position, orientation and/or size of the box which defines the bounds of the reformat are be unconstrained. In some embodiments, the position, orientation and/or size of the box are constrained only by the size and shape of the image volume. For example, the box may lie primarily within the image volume.

In the present embodiment the protocol is for automatically constructing an oblique reformat displaying the shoulder. In other embodiments, the protocol may be for displaying any anatomical feature. More than one protocol may be stored in the registration circuitry 24. For example, protocols for viewing multiple joints may be stored. In some embodiments, a new protocol may be defined by a user and/or stored by the user in the registration circuitry 24. In some embodiments, further stages of the process of stage 2 may not require modification in order to automate a new protocol.

Information from the protocol is used in the processing of the imaging data set to obtain a respective view for each of the candidate transforms. We describe below the processing of the imaging data set to obtain a view for one of the candidate transforms. The processing described below is repeated for each of the candidate transforms. In other embodiments, a plurality of views may be obtained for each of the candidate transforms. For example, views may be obtained for each of a plurality of planes defined orthogonal to a principal axis of view. In some embodiments, the method of FIG. 2 may be used for multiple protocols, for example to obtain views of multiple, different anatomical features.

The registration circuitry 24 uses the candidate transform to transform the box defined by the protocol into the coordinate space of the imaging data set. Since the box is centred on the shoulder of the atlas, the transformed box may be expected to be at least approximately centred on the shoulder in the imaging data set.

The registration circuitry 24 selects an image patch using the coordinates of a target region in the box, defined in the atlas. The target region corresponds to the template. The registration circuitry 24 transforms the coordinates of the target region into the coordinate space of the imaging data set using the candidate transform. The registration circuitry 24 then samples the image patch at the mapped coordinates in the imaging data set.

The position, orientation and scale of the box in the imaging data set are based on the box defined by the protocol and on the candidate transform. The scaling may be anisotropic. A value for a scaling parameter for one axis may be different from a value for a scaling parameter from another axis.

The registration circuitry 24 processes the part of the imaging data set that is inside the box to obtain an oblique reformat view showing the target region, which in this embodiment is the centre plane of the box.

The registration circuitry 24 transforms the sampled image patch obtained at stage 38 into the coordinate space of the template. The transforming of the sampled image patch comprises scaling the sampled image patch. In the present embodiment, the image patch is an atlas-aligned, two-dimensional rectangle and the only transformation used in order to transform the image patch into the coordinate space of the template is scaling. In other embodiments, different transformations may be used.

The processing of the imaging data set to obtain a sampled image patch is performed for each of the candidate transforms.

Since the candidate transforms all have different parameter values, a different image patch is obtained for each of the candidate transforms. For example, different candidate transforms may result in image patches showing the shoulder from slightly different angles.

Figure 5:
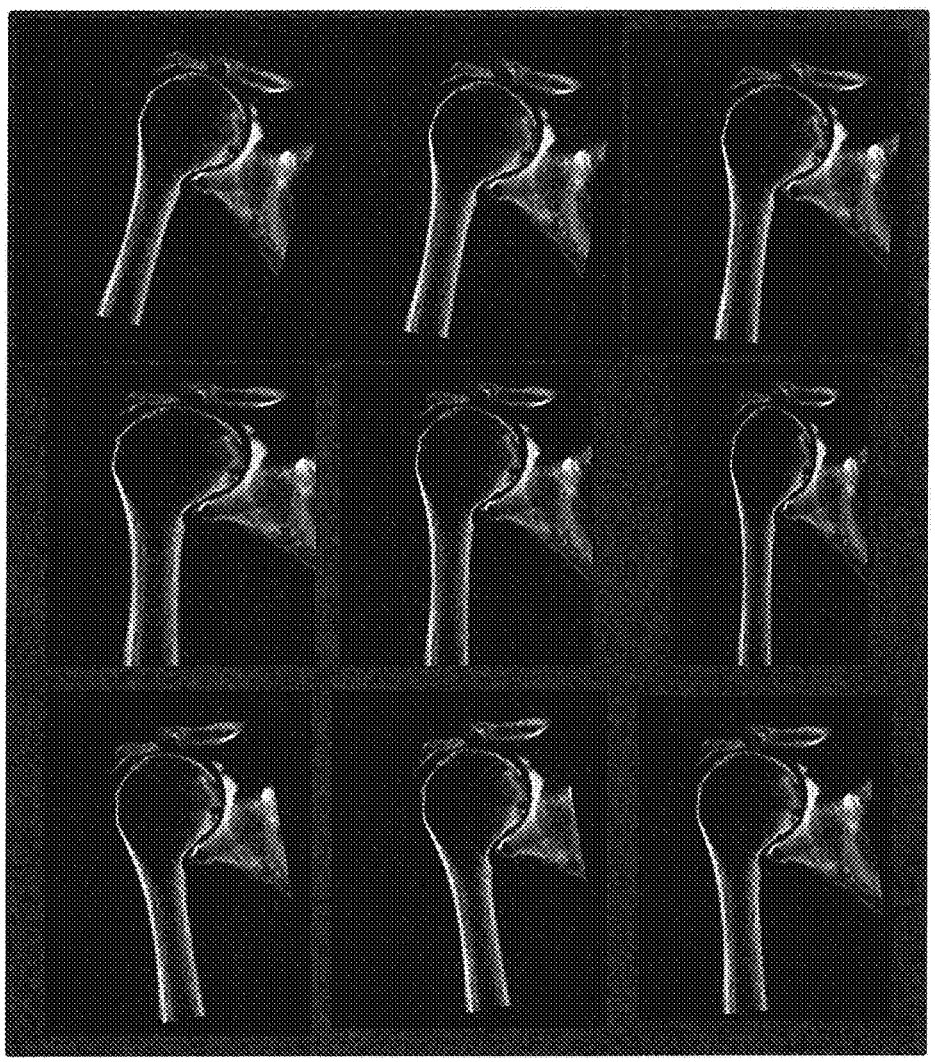
FIG. 5 comprises 9 oblique reformat images of a shoulder joint, the oblique reformat images having different orientations.

FIG. 5 shows an example of a plurality of image patches obtained for a plurality of different candidate transforms. Each candidate transform has different transform parameter values. In FIG. 5, the candidate transforms have different values for at least one rotation parameter. The image patches are therefore oblique reformats on different planes having different orientation. Some of the orientations may present a better view of the glenoid cavity than others of the orientations.

At stage 40, the matching circuitry 26 performs a template matching process to match a template with each of the image patches generated at stage 38. The template may also be referred to as a template image, template patch, or template image patch. The template is representative of a desired view of the shoulder.

It may be an aim of the process of FIG. 2 to obtain an oblique reformat view that shows the anatomy (in this case, the shoulder) from a desired orientation. In the present embodiment, the reformat may be intended to present the target anatomy to allow diagnosis from 2D images with a standard orientation. An image patch with the correct orientation may present the target anatomy such that the target anatomy has a specific shape. The template matching process may use this shape as a measure of the correctness of an orientation. In this embodiment, an image patch with a correct orientation may be an image patch that presents the shoulder such that the glenoid cavity is easily visible.

In the present embodiment, the template is an oblique reformat of the atlas. The template may be similar to the oblique reformat view shown in FIG. 4, in which the glenoid cavity is clearly visible. In other embodiments, any suitable template may be used. The template may show any suitable anatomy from any desired view.

The template matching process of stage 40 may be used to provide an improved view by matching each of the image patches to a template that is representative of the desired view. In some circumstances, the desired view may not be reliably obtained by registration alone. For example, simply generating a view using the most probable transform may not always produce an image that shows a good view of the desired anatomy, for example an image with a good view of the glenoid cavity. Variations between patients and/or differences in how the patient is positioned for scan may mean that the best registration does not provide the best view of the anatomy.

Figure 6:
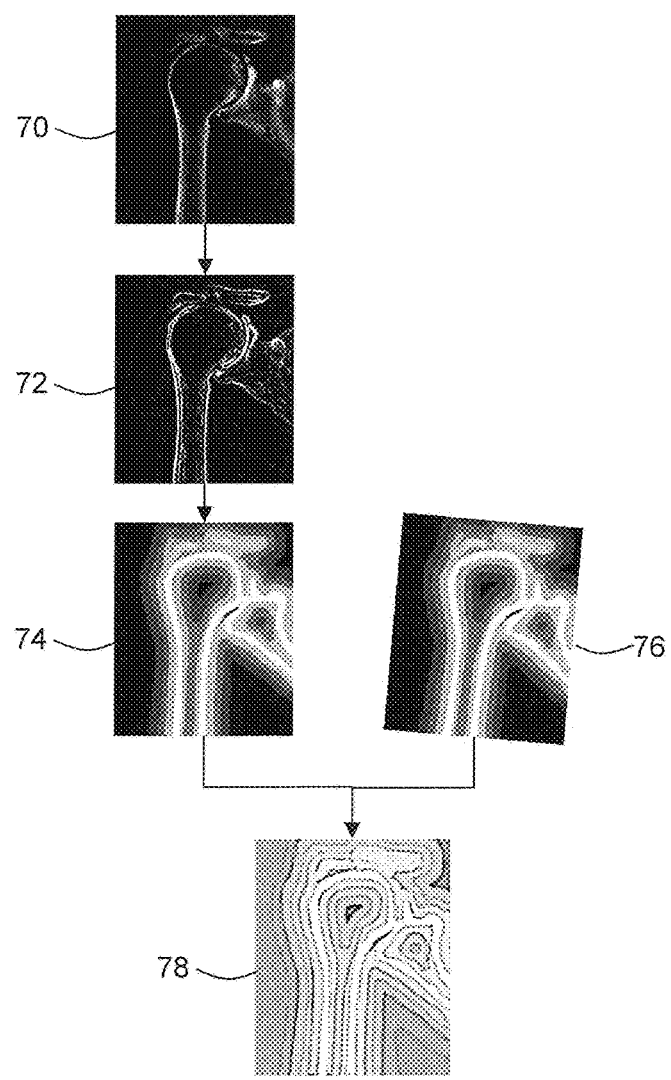
FIG. 6 is a flow chart illustrating in overview a method of matching an image and a template.

FIG. 6 is a flow chart which represents in overview the template matching process of the present embodiment. The template matching may be considered to measure the similarity of the image patch to the template.

At a first stage of the flow chart of FIG. 6, the matching circuitry 26 receives an image patch 70 from the registration circuitry 24. The matching circuitry 26 may also smooth the image patch 70, for example by applying a smoothing filter to reduce a noise level of the image.

At a second stage of the flow chart of FIG. 6, the matching circuitry 26 generates an edge map 72 by applying an edge filter to the image patch 70. The edge map comprises a plurality of edges which may be obtained using any suitable edge detection algorithm. In the present embodiment, the edges that are produced by the edge filter do not need to be closed contours.

At a third stage of the flow chart of FIG. 6, the matching circuitry 26 generates an edge distance map 74 from the edge map 72. In the present embodiment, each pixel of the edge distance map has a value that is representative of a distance between that pixel and the nearest edge in the edge map 72.

At a fourth stage of the flow chart of FIG. 6, the matching circuitry 26 subtracts the edge distance map 74 for the candidate image patch from an edge distance map 76 for the template.

In the present embodiment, the edge distance map 76 for the template is calculated once before the process of FIG. 2 is performed, and is stored by the matching circuitry 26. The edge distance map 76 for the template may be obtained from the template using a method similar to that described above for obtaining the edge distance map 74 for the image patch 70. An edge filter is applied to the template to obtain an edge map for the template. An edge distance map is then generated using the edge map for the template.

Subtracting the edge distance map for the image patch 70 from the edge distance map for the template results in a difference map 78. Each pixel in the difference map 78 has a value that is representative of the difference between the value of that pixel in the edge distance map 74 for the image patch 70, and the value of that pixel in the edge distance map 76 for the template.

The matching circuitry 26 determines a matching probability based on the difference map 78. In the present embodiment, the matching probability is the product of the sigmoid of each pixel in the difference map 78.

Let the template be T, and the candidate image patch determined by the candidate transform $\phi$ be $I_\phi$.

Let $D \circ E(I_\phi)$ be the result of a distance transform applied to an edge map for the image $I_\phi$. Now let $$L(i, j) = (D \circ E(I_\phi) - D \circ E(T))_{i,j}$$

be the loss at the i, jth pixel in $I_\phi$ given a template image, where $D \circ E(T)$ is the result of the distance transform applied to an edge map for the template T.

As the loss $L(i,j)$ is unbounded, let $$P(I_\phi | T) = \prod_{i,j} \sigma(L(i, j) \cdot \omega_{i,j})$$

where $\sigma$ is the sigmoid and $\omega_{i,j} \cdot \mathcal{N}(\mu_\omega; \sigma_\omega^2)$ is a gaussian weight.

The sigmoid $\sigma$ is the function $\sigma: \mathbb{R} \to [0,1]$ defined by $\sigma x = 1/(1+e^{-x})$ which smoothly maps the real numbers into the interval between 0 and 1.

The weight $\omega_{i,j}$ is over positions in the image patch and/or template. The weight is used in order to increase the significance of the loss at the most critical areas of the image. In the case in which the weight $\omega_{i,j}$ is a 3D Gaussian, the weight increases the significance of the loss at the centre of the patch (or decreases it at the edges). In other embodiments, more complex weighting schemes may be used. For example, a clinical expert may be asked to highlight the points, edges or regions which in their opinion are most determinative of the correctness of the view. The highest loss may be assigned at the points, edges or regions identified by the expert. The weighting may decrease with distance from those points, edges or regions.

$P(I_\phi|T)$ then provides a matching probability of the image patch $I_\phi$ given the template T, where the matching probability is a value between 0 and 1. The calculation of $P(I_\phi|T)$ may be considered to provide a normalisation step.

In some embodiments, the similarity metric used is the product of the sigmoid of the difference between the patch and the template at each pixel. In other embodiments, any similarity metric may be used, provided that the metric used can be normalised to a probability. In some embodiments, the similarity metric used may depend on the anatomy in question.

Performing the template matching on a distance transform applied to an edge map over the smoothed image patch may provide useful gradients.

The matching is used to align, as best as possible, a set of edges. A naïve approach to matching the edges, for example multiplying two binary edge elements together element wise, may not ascertain how close edges are to being correct if the edges do not match exactly. By using the edge distance maps, instead of the raw edges, the proximity of edges factors into the metric. An edge which lies at a distance of one from its correct position at every voxel will receive a high score even if it does not intersect the target edge at any point because it cumulative distance is still low; a highly dissimilar shape would however receive a low score under this metric, even if it intersected the target edge at significantly more points, by virtue of its distance at points outside of the intersection. Random noise which just happens to intersect at a few points will receive a low score reflecting the fact that its structure is unrelated to the template, irrespective of how many times the two intersect. Moreover, because this similarity admits of degrees, it may be considered to have a meaningful gradient. Changes to the transform parameters will smoothly change the value for the metric, which may allow an optimal change to be estimated using a small number of samples. Metrics which are not smooth in this way (for example, a naïve intersection method) may not have well defined gradients, so samples may provide no information about how the metric changes as the underlying parameters are changed.

In further embodiments, the template matching process may not comprise obtaining an edge map and/or distance transform.

The template matching process is performed for each of the image patches that were obtained at stage 38.

A last step in evaluating each candidate transform is to compute the probability of the match for that candidate transform, given the prior information from the landmarks.

At stage 42, the matching circuitry 26 determines a joint probability for each candidate transform using the registration probability distribution determined at stage 32 in combination with the matching probability determined at stage 40. The joint probability for the candidate transform comprises the probability of matching the image patch for that candidate transform and the template, given as a prior probability the registration probability for the candidate transform.

Formally, let:

$\theta$ denote the transform parameters (note that both the transformation as a function and the parameterisation of that function were previously denoted by $\phi$ above);

$L_D$ denote the detected landmark positions (denoted as x above;

$L_A$ denote the atlas landmark positions (denoted as y above;

$I_T$ denote the template image patch;

$I_\theta$ denote the candidate image patch for $\theta$.

The posterior probability that the candidate transform is correct, given the template match and the landmark registration may then be expressed as:

$$p(\theta | I_T, I_\theta, L_D, L_A) = \frac{p(I_\theta, L_D | \theta, I_T, L_A) p(\theta | I_T, L_A)}{p(I_\theta, L_D)}$$

$$\propto p(I_\theta, L_D | \theta, I_T, L_A) p(\theta | I_T, L_A)$$

On the assumption that the landmarks and template match are conditionally independent given the transform, the joint probability $p(I_\theta, L_D | \theta, I_T, L_A)$ of the template match and the detected landmarks decomposes into the product of the probability of the template match $p(I_\theta | \theta, I_T)$ and the detected landmarks $p(L_D | \theta, L_A)$, hence:

$$p(\theta | I_T, I_\theta, L_D, L_A) \propto p(I_\theta | \theta, I_T) p(L_D | \theta, L_A) p(\theta | I_T, L_A) \propto p(I_\theta | \theta, I_T) p(L_D | \theta, L_A) p(\theta)$$

where the last line follows from the fact that the prior $p(\theta | I_T, L_A)$ on the transform is independent of the template or atlas landmarks.

The prior $p(\theta)$ represents the probability distribution over transforms in the absence of any information about the specific volume. In some embodiments, the prior $p(\theta)$ is modelled as a Gaussian. For example, if the likelihood is modelled as a Gaussian, modelling the prior as a Gaussian may result in simpler mathematics.

If the prior $p(\theta)$ is modelled as a Gaussian, it may be described by two parameters: a mean value and a variance.

It may be expected that a most probable transform from an atlas to a novel volume may be close to identity (the transform which maps every point to itself). Therefore, in some embodiments, identity is chosen a mean, and a small translation, rotation and scale is chosen as a variance.

In some embodiments, the prior $p(\theta)$ over transforms, ignoring landmarks, may be inferred from the training set for that reformat. In some embodiments, the prior may be the maximal probability distribution for the landmarks. Ground truth may be known for sets of training data. A correct transformation for each set of training data may be obtained using the ground truth, and the mean and variance of the transformations may be taken to define the prior $p(\theta)$.

Once a respective joint probability has been calculated for each of the candidate transforms, the matching circuitry 26 selects the one of the candidate transforms having the highest joint probability. The one of the candidate transforms having the highest joint probability may be considered to provide the best match to the template.

Stages 36 to 42 may be described as a selection process. The selection process comprises generating candidate transforms, matching an image patch generated from each candidate transform to the template to obtain a joint probability, and selecting the one of the candidate transforms having the highest joint probability.

At stage 44, the registration circuitry 24 determines whether the joint probabilities have converged. If the joint probabilities have not converged, the flow chart of FIG. 2 returns to stage 36.

In the present embodiment, multiple iterations of the selection process of stages 36 to 42 are performed. In each iteration, new candidate transforms are obtained by sampling parameter values neighbouring the parameter values for the candidate transform having the highest joint probability according to the previous iteration, which may be described as the current best candidate transform. The matching circuitry 26 evaluates the template matching for the current best candidate transform and its neighbours. The matching circuitry 26 combines the template matching probability with the prior probability for each candidate transform under the distribution that was determined at stage 32.

The matching circuitry computes the joint probability for the image patch (matching the template) and the detected landmarks (matching the reference landmarks) under the candidate transform, $p(I_\theta, L_D | \theta, I_T, L_A)$. The calculation of the joint probability may be considered to provide a means of integrating the two estimates of the match, from the landmarks and from the templates. The matching circuitry 26 then selects a new most probable candidate transform based on the joint probabilities. At the end of each selection process, the flow chart proceeds to stage 44 where the registration circuitry 26 decides whether to perform a further selection process.

Stages 36 to 44 are repeated until the joint probabilities converge. In the present embodiment, he joint probabilities may be considered to converge if the candidate transform having the highest joint probability remains substantially the same from one iteration to the next, for example if the generation of a new set of candidate transforms from the candidate transform having the highest joint probability does not produce any new candidate transform that has a higher joint probability. In other embodiments, any suitable convergence criterion may be used.

In some embodiments, the iterative search process of stages 36 to 44 comprises a gradient descent search. The distribution of registration probabilities obtained at stage 32 constrains the gradient descent search for an optimal template match. The construction of the joint probability gives a gradient which informs the search. By using the distribution of registration probabilities, a number of candidate transforms that is searched may be reduced.

In some embodiments, the descent may be considered to have converged if the improvement in probability falls below a threshold value. The threshold value may be empirically determined. For example, some sampling methods may take progressively smaller and smaller steps. By setting a threshold value, it may be possible to avoid spending a large number of iterations evaluating new candidates which may be considered to be functionally, but not strictly, identical to an existing candidate.

At stage 46, the matching circuitry 26 selects the candidate transform at which the joint probability converged. The display circuitry 28 receives the image patch that was previously generated using the selected candidate transform and displays that image patch on the display 16. In other embodiments, the display circuitry 28 may generate the image patch using the selected candidate transform.

The displayed image displays the anatomy (in this case, the shoulder) from a desired orientation, for example from a standard orientation that is used in diagnosis.

For simplicity, we have described an embodiment in which a single image patch is generated for each candidate transform. In other embodiments, a series of image patches may be produced for each candidate transform. For example, the image patches may be generated on planes sampled along the principal axis of the reformat bounding box. The series of image patches may be displayed to the user at stage 46.

By selecting a transform (and therefore a view) using a combination of registration probability and matching probability, a view may be obtained that is closer to a desired view than a view that is obtained using registration alone. The similarity to the template of a shape of the anatomy as shown in the view may be used as a measure of the correctness of the transform used to produce that view.

The notion of similarity of a view may be determined by the relationships between anatomical structures, and hence relative to each patient. Where the relationship between anatomical structures can change, it may be considered to be relative to a patient at a particular time.

The method of FIG. 2 may provide automatic reconstruction of views which may otherwise be difficult and/or time consuming to produce. For example, it may sometimes take even an experienced radiographer several minutes to align imaging data to produce a desired view.

In some circumstances, the time and/or processing power used to produce the view may be less than if an attempt were made to provide automated reconstruction by performing template matching without first performing a registration. The probability distribution may be used to reduce the number of candidate transforms that are computed and evaluated. A sequence of candidates may be selected starting from the most probable under the probability distribution.

A search space of possible template orientations and positions may be very large, with many local minima, which may make an exhaustive search difficult or impossible. Fixed shape templates may not account for inter-patient differences. By first using a registration process and then performing template matching using transforms obtained from the registration process, the search space of possible template orientations and positions may be limited. By allowing scaling, inter-patient differences may be taken into account.

In the embodiment of FIG. 2, landmarks detected in the input are registered to landmarks in an atlas. The registration process uses a linear model. The use of a registration process comprising landmark registration may make it possible to compute not just a single transform, but a distribution over transforms. The distribution over transforms may be used to guide the template search.

By computing an affine transform from landmark registration, the template image may be anisotropically scaled at each candidate position, which may allow inter-patient differences to be taken into account.

In the method of FIG. 2, the registration probability is not simply used to initialise the process of template matching. Instead, the registration probability is used in combination with the template matching probability. By keeping the registration probability in the later stages of the process, it may be the case that accuracy and/or speed are improved.

In some circumstances, the method of FIG. 2 may not require modification to automate a new protocol. In some circumstances, the method of FIG. 2 may be used for any protocol and template that is input to the method, if the protocol or template is suitable for a target anatomy. Other stages of the method (for example, the registration process and template matching process) may not be specific to any particular anatomy. It may in some circumstances be straightforward to apply the method of FIG. 2 to different anatomies and/or different views.

In some embodiments, a template may be based on one or more images that have been selected by a user as being representative of a desired view of the anatomy. The template may be derived from an atlas or from other reference data. The template is defined in the same space as the reference landmarks so that a registration to the reference landmarks also serves as a registration to the template.

In some embodiments, a template is based on a plurality of images that have previously been produced by an expert, for example oblique reformat images that have previously been produced manually by one or more radiographers.

In some circumstances, different clinicians may have different preferences for the exact view that it is used to visualise particular anatomy. Therefore, in some embodiments, more than one template may be stored for a particular anatomical feature (for example the shoulder). The different templates may be representative of the different preferred views of different clinicians. When producing a view for a particular clinician, the preferred template for that clinician may be used.

In some embodiments, a template is produced by a training process comprising acquiring a plurality of views that have been selected and/or used by an individual clinician (for example, an individual radiologist) and processing the plurality of views to obtain a template view. In some such embodiments, landmarks are combined for volumes from which the plurality of views were taken. Any suitable method of combination of landmarks may be used. For example, an average of landmark positions may be used in circumstances where the difference between patients can be well modelled with a simple affine transformation.

In the embodiment of FIG. 2, the template is a 2D image. In other embodiments, the template may be three-dimensional. The protocol may generate three-dimensional regions of the imaging data from the candidate transforms. The template may be matched to three-dimensional regions of the imaging data.

In some embodiments, the method of FIG. 2 may be performed with multiple different templates to obtain multiple different views of the same imaging data.

In some embodiments, a single view may be obtained using more than one template. For example, where the anatomy to be visualised is a joint between two bones, two templates may be used. A first template may show a desired view of the first bone and a second template may show a desired view of the second bone. A respective template matching probability may be obtained for each of the templates. A registration and/or view may be selected by combining both of the template matching probabilities and the registration probability.

In some embodiments, a parts-based poly-affine model is used to combine templates. The anatomy is modelled as a set of boxes, each of which is registered independently. An additional model for each pairs of connected components describes the weighting of orientations of those parts in determining the orientation of a view which is centred in between them. In some embodiments, the weighting comprises the ratio of overlap with each component. In some embodiments, the weighting is based on the physical properties of the connecting tissue.

The method of FIG. 2 provides automated reconstruction of oblique views. In the process of FIG. 2, an oblique reformat view is obtained and displayed on the display 16. In other embodiments, no view is displayed at the end of the method of FIG. 2. In some embodiments, stage 46 is omitted. The selected transform and/or the oblique reformat view obtained using the selected transform may be stored, or may be used in performing a further process. In some embodiments, the method of FIG. 2 is implemented on a computing apparatus without a display, or any hardware intended for the production or manipulation of graphical data.

In some embodiments, an output of the method of FIG. 2 is a transformation matrix specifying one or more target views.

In some embodiments, automatically reconstructed oblique views are used for export as a derived series. In some circumstances, not all of the medical imaging data obtained from a medical imaging scan may be stored in a PACS. Instead, a choice may be made of which data to keep. For example, a set of thicker slices may be stored instead of storing a set of thin slices that were originally acquired. In some embodiments, the selected oblique reformat view may be stored as part of the data stored in the PACS.

In some embodiments, an oblique reformat is performed automatically before being sent to PACS. In some circumstances, the automatic reformat may obviate a need to store the original data, or manipulate it later.

In some embodiments, an oblique reformat is performed as part of an anticipatory processing method, for example a method in which all algorithms applicable to a scan are applied immediately after acquisition of that scan.

In some embodiments, a computing apparatus determines that a scan is of an appropriate type to generate a set of oblique reformats. The reformats are then generated automatically. In some embodiments the computing apparatus is a backend server. In some embodiments, the computing apparatus has no user interface.

In some embodiments, large quantities of stored data may be analysed, and oblique reformats are automatically generated for any data set for which oblique reformats are considered to be appropriate, for example any data set showing an appropriate joint.

In some embodiments, an automatically reconstructed oblique reformat view is used as an alignment tool in an interactive 3D application. For example, a 3D image may be initially displayed at an orientation that is in accordance with the selected transform. The user may then adjust the orientation manually.

In many different embodiments, the method of FIG. 2 (with or without the final stage 46 of displaying an image) may be used to locate and orient 2D images in a 3D space. The 2D images may be considered to be arbitrary. The 2D images may be representative of any appropriate anatomy at any location within the body. In some embodiments, the locating and orienting of the 2D images may be based only on detectable landmarks and an appearance of a template.

In some embodiments, the method of FIG. 2 is used for finding bounding planes in scan planning. In some circumstances, it may be undesirable for a medical scan to be set up manually. Automatic setup of a scan may be preferred. For example, automatic tilting of a gantry may be used. In some cases, there may be a preference for data to be acquired such that the data is axis-aligned, for example because reformatting the data with rotation may lose some accuracy. The method of FIG. 2 may be performed on a set of initial scan data (for example, from a pilot scan), to determine bounding planes for a subsequent scan, such that the orientation of the scan is suitable for obtaining a desired view from axis-aligned data.

In some embodiments, the method of FIG. 2 is used to align imaging data input to algorithms that are not orientation invariant. For example, image patches may be obtained and reoriented using the method of FIG. 2 and input into a convolutional neural network.

In some embodiments, the method of FIG. 2 may be used to perform registration of partially 3D data (for example, non-volumetric MRI data) to a 3D atlas. Registration may be performed by localising the plane in the atlas instead of the input.

The algorithm as presented with reference to FIG. 2 uses two sets of images, at least one of which is volumetric. Image patches are rotated to match a template. The dataset used as the atlas (which is the source of the template) may be two-dimensional provided that landmarks can be registered.

In further embodiments, an atlas data set comprises a plurality of slices. Existing three-dimensional data is registered to the atlas data set. For example, each slice of the atlas data set, or a patch in the centre of each slice, may be used as a template. By registering the three-dimensional data set to the atlas (rather than registering an atlas or template to the three-dimensional data set), a robust form of 2D to 3D registration may be provided.

Given 3D data, a 2D template may act as a constraint which the data can be transformed to better match by rotating it to lie in the same plane, and orientation in that plane.

In some circumstances, a case in which the atlas is 2D and the input is 3D may not be significantly more complicated than a 3D to 3D case as described above, provided that the landmarks can be registered, as the only imaging data drawn from the atlas is the template, which is 2D.

A more complex case may be matching 2D input data with an existing 3D volume. For this, it may be possible to generate a registration by applying the method above in reverse. Instead of searching for a match of a predefined template in a 3D atlas, we may define the template dynamically in the 2D input image by taking the centre of the input as the template, and then searching the atlas for a patch which matches this input template. Again this may depend on having functional detection of landmarks in 2D. In some circumstances, it may be difficult to detect the landmarks in 3D. A specific view to be reconstructed may be the view that is captured in the input image, as opposed to anything one might define in the atlas.

In the embodiments described above, three-dimensional imaging data is registered to atlas data. In other embodiments, two-dimensional imaging data may be registered to atlas data using a similar method to that described above with reference to FIG. 2.

Given 2D imaging data, the range of possible transforms is much reduced. It may be difficult to satisfy the constraint provided by the template unless the template and the 2D imaging data were captured from the same or similar plane. In some embodiments, the projection may be accounted for the template matching.

Certain embodiments provide a method for the automatic alignment of medical images by template search guided by a probability distribution derived from landmark registration. The method may be as follows:

1. detect landmarks in the input volume;
2. compute a probability distribution over the transforms from the detected landmarks to an atlas;
3. starting with the most probable transform, until converged:
   3.1. compute new candidate transforms neighbouring the current most probable transform;
   3.2 for each candidate transform:
      3.2.1 compute the candidate image patch determined by that transform;
      3.2.2. compute the probability that the patch matches the template image patch in the atlas;
      3.2.3 compute the probability of the match given the prior probability on the transform determined by landmarks;
   3.3 if no new candidate has a higher probability than the current one, then we have converged, else select the most probable candidate for the next iteration.

The transforms considered may be general affine, allowing anisotropic scaling. The candidate image patch may be anisotropically scaled under the transform to better match the template.

The resulting method may be as follows:
1. detect landmarks in the input volume;
2. compute a probability distribution over the affine transforms from the detected landmarks to an atlas;
3. starting with the most probable transform, until converged:
   3.1 compute new candidate transforms neighbouring the current most probable transform;
   3.2 for each candidate transform:
      3.2.1 compute the candidate image patch determined by that transform, taking anisotropic scaling into account;
      3.2.2 compute the probability that the patch matches the template image patch in the atlas;
      3.2.3 compute the probability of the match given the prior probability on the transform determined by landmarks;
   3.3. if no new candidate has a higher probability than the current one, then we have converged, else select the most probable candidate for the next iteration.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus comprising processing circuitry configured to:
   obtain medical imaging data that is representative of an anatomical region of a subject, the anatomical region comprising at least one anatomical feature of interest;
   obtain a template that is representative of a desired view of the at least one anatomical feature of interest;
   register the medical imaging data and reference anatomical data to obtain a distribution of registration probability with respect to at least one registration parameter; and
   perform a selection process comprising:
      obtaining a plurality of transforms, each having an associated registration probability;
      for each of the plurality of transforms:
         generating a respective view of the at least one anatomical feature of interest based on said transform; and
         determining a template matching probability that represents a similarity of the generated view to the template; and
      selecting at least one of the transforms and/or at least one of the views based on a combination of at least one of the registration probabilities with at least one of the template matching probabilities.

2. An apparatus according to claim 1, further comprising a display device, wherein the processing circuitry is further configured to display the selected at least one view on the display device.

3. An apparatus according to claim 1, wherein the selection process comprises obtaining the plurality of transforms based on the distribution of registration probability.

4. An apparatus according to claim 1, wherein the obtaining of the plurality of registrations comprises selecting a transform having a highest registration probability, and adjusting at least one registration parameter of the selected transform to obtain further registrations.

5. An apparatus according to claim 1, wherein selecting at least one of the registrations and/or at least one of the views based on a combination of at least one of the registration probabilities and at least one of the template matching probabilities comprises selecting the at least one of the registrations and/or at least one of the views based on a joint probability for each of the plurality of registrations.

6. An apparatus according to claim 1, wherein the processing circuitry is further configured to perform a plurality of iterations of the selection process.

7. An apparatus according to claim 6, wherein each iteration of the selection process comprises:
   obtaining a plurality of further transforms based on at least one transform and/or view selected in the previous iteration;
   for each of the plurality of further transforms:
      generating a respective view of the at least one anatomical feature of interest based on said further transform; and
      determining a template matching probability that represents a similarity of the generated view to the template; and
   selecting at least one of the plurality of further transforms and/or at least one of the views generated from the further transforms based on a combination of at least one of the registration probabilities for the further transforms with at least one of the template matching probabilities for the further transforms.

8. An apparatus according to claim 6, wherein processing circuitry is configured to perform the iterations of the selection process until a convergence condition is met.

9. An apparatus according to claim 1, wherein the distribution of registration probabilities is used to guide a search over candidate transforms.

10. An apparatus according to claim 9, wherein the search over candidate transforms comprises a gradient descent search.

11. An apparatus according to claim 1, wherein each respective view of the at least one anatomical feature comprises a respective oblique reformat.

12. An apparatus according to claim 1, wherein each transform comprises an affine transform.

13. An apparatus according to claim 1, wherein at least some of the transforms each comprise anisotropic scaling.

14. An apparatus according to claim 1, the registering of the medical imaging data and the reference anatomical data comprising mapping a plurality of landmarks in the medical imaging data with corresponding reference landmarks in the reference anatomical data.

15. An apparatus according to claim 1, wherein the reference anatomical data comprises at least one of: atlas data, virtual anatomy data.

16. An apparatus according to claim 1, wherein, for each transform, the determining of the template matching probability for said transform comprises obtaining a distance map of the respective view by locating at least one edge within the view image and determining, for each of a plurality of pixels in the view, a distance to the at least one edge, and comparing the distance map of the respective view with a distance map of the template.

17. An apparatus according to claim 1, wherein the at least one anatomical feature of interest comprises a joint.

18. An apparatus according to claim 17, wherein the joint comprises at least one of a knee, a shoulder, an elbow, a wrist, an ankle, a hip joint.

19. An apparatus according to claim 1, wherein the medical imaging data comprises at least one of CT data, cone-beam CT data, MR data, X-ray data, ultrasound data, PET data or SPECT data.

20. A method comprising:
   obtaining medical imaging data that is representative of an anatomical region of a subject, the anatomical region comprising at least one anatomical feature of interest;
   obtaining a template that is representative of a desired view of the at least one anatomical feature of interest;
   registering the medical imaging data and reference anatomical data to obtain a distribution of registration probability with respect to at least one registration parameter; and
   performing a selection process comprising:
   obtaining a plurality of transforms, each having an associated registration probability;
   for each of the plurality of registrations:
      generating a respective view of the at least one anatomical feature of interest based on said transform; and
      determining a template matching probability that represents a similarity of the generated view to the template; and
   selecting at least one of the transforms and/or at least one of the views based on a combination of at least one of the registration probabilities with at least one of the template matching probabilities.

\* \* \* \* \*